US00PP15664P3

(12) United States Plant Patent

Brljevich et al.

(10) Patent No.: US PP15,664 P3
(45) Date of Patent: Mar. 15, 2005

(54) VARIETY OF CALLA LILY NAMED 'SWAN LAKE'

(50) Latin Name: *Zantedeschia sprengeri*
Varietal Denomination: Swan Lake

(75) Inventors: Trevor Brljevich, Northland (NZ); Yvonne Brljevich, Northland (NZ)

(73) Assignee: W & J Gravatt, Waipu (NZ)

( * ) Notice: Subject to any disclaimer, the term of this patent is extended or adjusted under 35 U.S.C. 154(b) by 0 days.

(21) Appl. No.: 10/423,333

(22) Filed: Apr. 25, 2003

(65) Prior Publication Data

US 2004/0216199 P1 Oct. 28, 2004

(51) Int. Cl.[7] ..... A01H 5/00

(52) U.S. Cl. ..... Plt./263

(58) Field of Search ..... Plt./263

(56) References Cited

PUBLICATIONS

GTITM UPOV ROM Citation for 'Swan Lake' as per NZ PBR ZAN021; Jun. 26, 2001.*

* cited by examiner

*Primary Examiner*—Kent Bell
*Assistant Examiner*—Louanne Krawczewicz Myers
(74) *Attorney, Agent, or Firm*—Webb Ziesenheim Logsdon Orkin & Hanson, P.C.

(57) ABSTRACT

'Swan Lake' is a new variety of calla lily having beautiful white flowers and strong branching.

2 Drawing Sheets

Botanical classification: *Zantedeschia sprengeri.*
Varietal denomination: 'Swan Lake'.

BACKGROUND OF THE NEW PLANT

The present invention comprises a new and distinct cultivar of calla lily, botanically known as *Zantedeschia sprengeri* and hereinafter referred to by the cultivar name 'Swan Lake'.

'Swan Lake' was discovered in 1996 and chosen from a selection of seedling tubers of unknown parentage in Maungaturoto, New Zealand. The first act of asexual reproduction of 'Swan Lake' by tissue culture was performed in 1997 in Auckland, New Zealand. Subsequent asexual reproductions by tissue culture have demonstrated that the combination of characteristics as herein disclosed for the new cultivar are retained through successive generations of asexual reproduction and reproduces true to type.

The following traits have been repeatedly observed and determined to be basic characteristics of 'Swan Lake' which, in combination, distinguish this calla lily as a new and distinct cultivar:

1. 'Swan Lake' has fewer leaf maculations than 'Black Eyed Beauty' (unpatented), 'Albomaculata' (unpatented), 'Starlight' (unpatented), and 'Chromatella' (unpatented);
2. 'Swan Lake' is taller than 'Innocence' (unpatented);
3. 'Swan Lake' has a longer spathe of smaller diameter than 'Starlight' and 'Chromatella'; and
4. 'Swan Lake' has a distinctive purple-brown coloring overlay near the tip of the outside of the spathe as the spathe becomes older and the seed pod develops.

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

Figure 1:
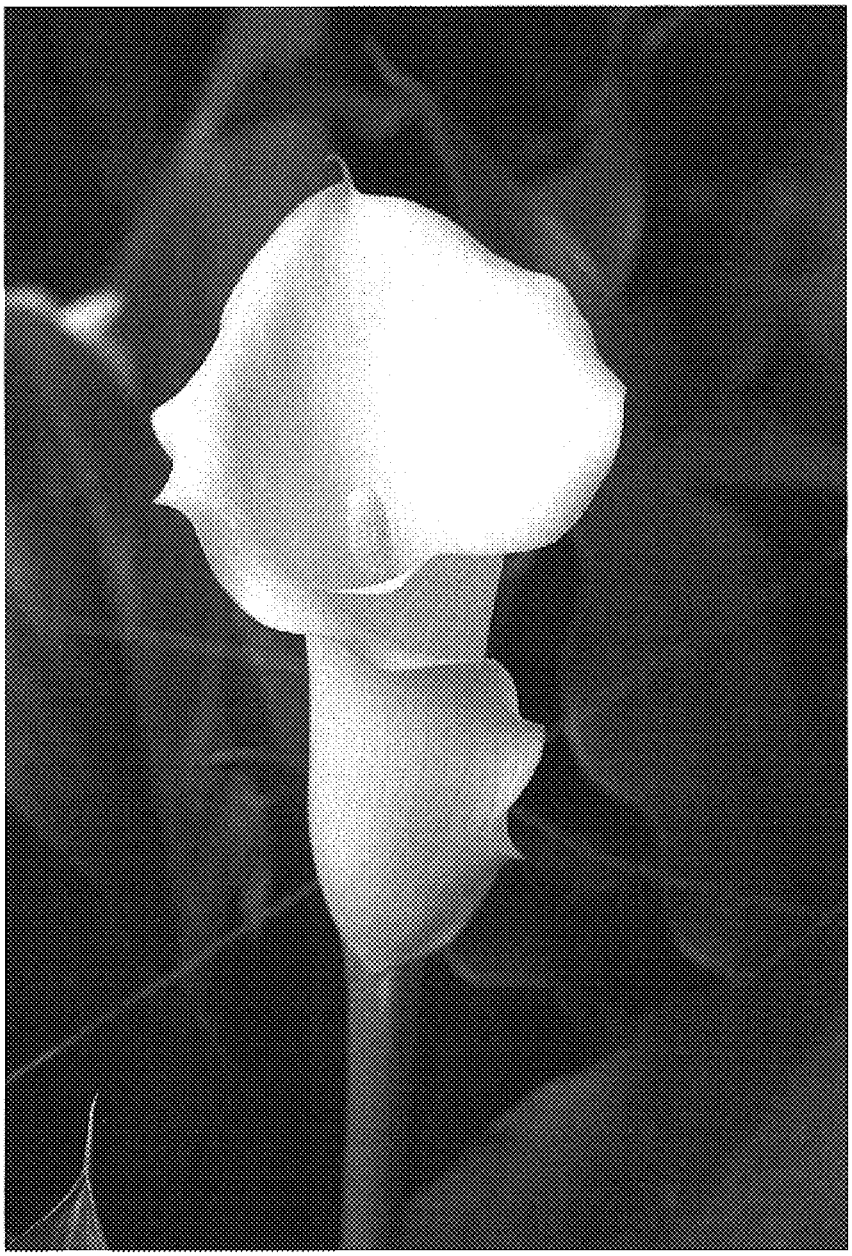
FIG. 1 is a close-up photograph of a flower of the new variety.
Figure 2:
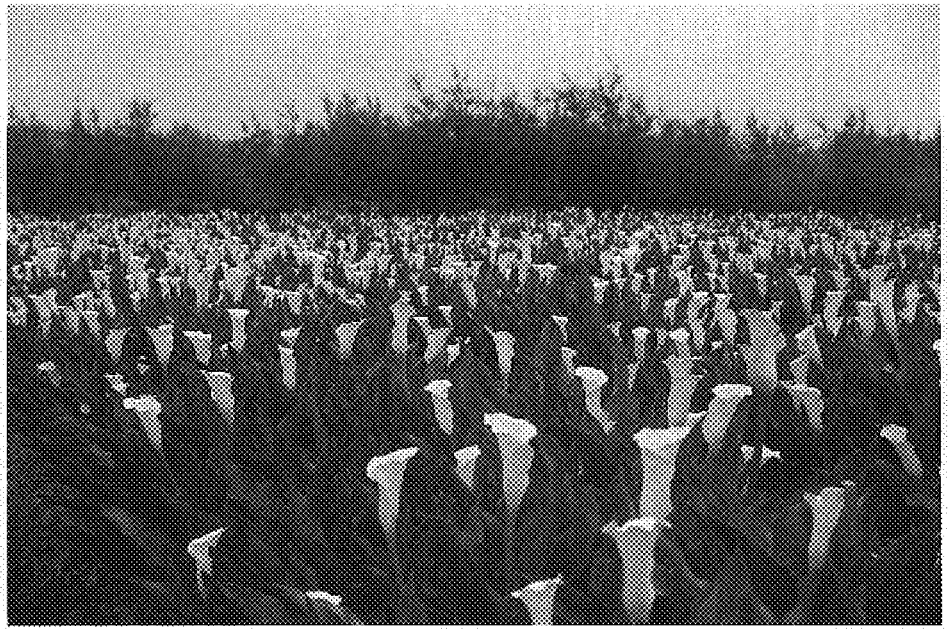
FIG. 2 illustrates a field of flowers of the new variety.

The following observations, measurements, and comparisons describe plants grown in New Zealand under conditions which approximate those generally used in horticulture practice. The field grown plants were 16 weeks into their third growing cycle when described. Color references are made to the R.H.S. Colour Chart of The Royal Horticultural Society of London, except where general color terms of ordinary significance are used.

THE PLANT

Size:
- *Height of the leaf canopy above the soil.*—500–900 mm; Average of 600 mm.
- *Height of top of flowers above the soil.*—500–1000 mm; Average of 700 mm.
- *Diameter.*—200–600 mm; Average of 500 mm.
- *Form.*—Erect.

Number of flowers per tuber size:
- *Diameter of 3–4 cm.*—2–4 flowers.
- *Diameter of 4–5 cm.*—4–6 flowers.
- *Diameter of 5 or more cm.*—4–10 flowers.

Branches:
- *Character.*—Strong.
- *Color.*—147A.
- *Number.*—3–6 per plant.

Leaves:
- *Size.*— Width: 100–180 mm; Average of 130 mm. Length: 200–400 mm; Average of 300 mm.
- *Shape.*—Deltoid.
- *Apex.*—Apiculate to slightly rounded at the point of the apex.

*Base.*—Rounded at the corners and smooth, but slightly ruffled along the base.

*Margin.*—Smooth, but slightly ruffled with a color of 150A.

*Number per plant.*—6–15.

*Color.*—Upper surface: 147A, streaked with 144A. Lower surface: 146A, streaked with 144A.

*Spotting or mottling.*—Description: 10–70 maculations per leaf, ranging from 1 mm dots to 1 mm×8 mm long lines that follow the direction of the leaf venation. Appearance: Transparent, like a small window in the leaf. The mottling is caused by a small break in the green chlorophyll. There is no color.

*Veins.*—Configuration: Pinnate. Color: 144A.

*Surface quality.*—Leathery.

Petiole:

*Length.*—200–650 mm; Average of 450 mm.

*Diameter.*—8–15 mm.

*Color.*—144D with striations of 177A at the base of the petiole, changing to 144A up the length of the petiole.

Roots:

*Color.*—White.

*Branching.*—Moderate.

THE FLOWER

Spathe:

*Size.*—Length: 70–130 mm; Average of 90 mm. Width: 40–80 mm; Average of 70 mm.

*Color.*—Inner surface: 150D. Outer surface: Base of spathe is 144C, changing to 150D. As the spathe ages and the seed pod ripens, the spathe turns a combination of 144A and 144B, with an overlay of 177A near the tip of the spathe.

*Veins.*—Appearance: Transparent. The veins are a break in the pigmentation of the flower. Configuration: Parallel. Shape: Overall: Cupped and ruffled. Tip: Pointed. Base: Cylindrical and widening distally.

*Spadix.*—Size: Length: 35–65 mm. Diameter: 5–12 mm. Color: 12A. Mature and immature Reproductive Organ Color: Male: 12A. Female: 150C. Position relative to spathe: Upright.

*Peduncle.*—Size: Length: 300–900 mm; Average of 500 mm. Diameter: 8–15 mm. Color: 144D with 177A striations at the base of the peduncle, changing to 144A striations through the rest of the peduncle.

*Reproductive organs.*—Location of female organs: Basal position of the spadix (lower 35%). Location of male organs: Upper position of the spadix (upper 65%). Stamens: Not visible before pollen release. Pistil: Average number: 30. Length beyond perianth: 0.5 mm. Shape: Dome.

*Flowering.*—Tubers planted in New Zealand begin to produce flowers 85 days after planting and continue to flower over a 20–30 day period.

*Lastingness.*—Cut flowers last 5–14 days. On the plant stem, emergence to senescence is 19–22 weeks.

*Fragrance.*—None.

*Fruit.*—Size of individual seed pod: 10–12 mm in diameter. Appearance of seed pod: Rounded and wrinkled. Color of seed pod: 144A fading to 144D at the base of the seed pod.

*Seeds.*—Shape: Oval and Rounded. Length: 5–7 mm. Diameter: 4–5 mm. Color: 145C.

*Disease resistance.*—High.

*Pest resistance.*—Strongly attractive to Thrips.

I claim:

1. A new and distinct cultivar of calla lily plant named 'Swan Lake', as described and illustrated herein.

* * * * *